(12) United States Patent
Friedman et al.

(10) Patent No.: US 6,537,291 B2
(45) Date of Patent: Mar. 25, 2003

(54) METHOD FOR DETECTING A LOOSE BLADE IN A HAND PIECE CONNECTED TO AN ULTRASONIC SURGICAL SYSTEM

(75) Inventors: Allan L. Friedman, Cincinnati, OH (US); Foster B. Stulen, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/870,989

(22) Filed: May 31, 2001

(65) Prior Publication Data

US 2002/0049463 A1 Apr. 25, 2002

Related U.S. Application Data

(60) Provisional application No. 60/241,892, filed on Oct. 20, 2000.

(51) Int. Cl.⁷ .............................................. A61B 17/32
(52) U.S. Cl. ...................................................... 606/169
(58) Field of Search ................................ 606/167, 169, 606/168, 178

(56) References Cited

U.S. PATENT DOCUMENTS

| | | | |
|---|---|---|---|
| 2,917,691 A | 12/1959 | DePrisco et al. | |
| 5,001,649 A | 3/1991 | Lo et al. | |
| 5,026,387 A | 6/1991 | Thomas | |
| 5,112,300 A | 5/1992 | Ureche | |
| 5,180,363 A | 1/1993 | Idemoto et al. | |
| 5,400,267 A | 3/1995 | Denen et al. | |
| 5,425,704 A | 6/1995 | Sakurai et al. | |
| 5,449,370 A | 9/1995 | Vaitekunas | |
| 5,630,420 A | 5/1997 | Vaitekunas | |
| 5,707,369 A | 1/1998 | Vaitekunas et al. | |
| 5,879,364 A | 3/1999 | Bromfield et al. | |
| 5,968,007 A | 10/1999 | Simon et al. | |
| 6,017,354 A | 1/2000 | Culp et al. | |
| 6,019,775 A | 2/2000 | Sakurai | |
| 6,051,010 A | * 4/2000 | DiMatteo et al. | 604/22 |
| 6,053,906 A | * 4/2000 | Honda et al. | 606/1 |
| 6,066,135 A | 5/2000 | Honda | |
| 6,090,123 A | 7/2000 | Culp et al. | |
| 6,332,891 B1 | * 12/2001 | Himes | 606/130 |

FOREIGN PATENT DOCUMENTS

JP   2000-175926   6/2000

* cited by examiner

*Primary Examiner*—Ismael Izaguirre
(74) *Attorney, Agent, or Firm*—Darby & Darby (57) ABSTRACT

A method for detecting loose blades in a hand piece connected to an ultrasonic surgical system by performing frequency sweeps of a drive signal through a range which includes the resonance of a hand piece/blade system and the resonance of the hand piece without a blade attached. The frequencies of resonance in each sweep are compared. If a substantial difference between the frequency sweeps occurs, then a "Tighten Blade" message is displayed on a liquid crystal display on an ultrasonic generator console. The method permits rapid and easy diagnosis of loose blade connections. The method also assists a surgeon or nurse in knowing when to tighten the blade, as opposed to performing more lengthy and detailed diagnostic or cleaning procedures. In addition, the time and costs associated with the diagnostic procedures to isolate faults are eliminated because, upon determining that the blade is not loose, the surgeon and/or nurse can request a new blade based on the assumption that the blade is broken.

10 Claims, 10 Drawing Sheets

METHOD FOR DETECTING A LOOSE BLADE IN A HAND PIECE CONNECTED TO AN ULTRASONIC SURGICAL SYSTEM

RELATED APPLICATIONS

The present invention relates to, and claims priority of, U.S. Provisional Patent Application Ser. No. 60/241,892 filed on Oct. 20, 2000, having the same title as the present invention, which is incorporated herein by reference.

BACKGROUND OF THE INVENTION

1. Field of the Invention

The present invention generally relates to ultrasonic surgical systems and, more particularly, to a method for detecting a loose blade on a hand piece connected to an ultrasonic surgical system.

2. Description of the Related Art

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations and the heat, as well as material fatigue resulting therefrom. In an operating room environment attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application and is incorporated herein by reference, discloses a system for controlling the heat in an ultrasonic surgical cutting and hemostasis system without the use of a coolant, by controlling the drive energy supplied to the blade. In the system according to this patent an ultrasonic generator is provided which produces an electrical signal of a particular voltage, current and frequency, e.g. 55,500 cycles per second. The generator is connected by a cable to a hand piece which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop (that includes a voltage controlled oscillator, a frequency divider, a power switch, a matching network and a phase detector), stabilizes the frequency applied to the hand piece. A microprocessor controls the amount of power by sampling the frequency, current and voltage applied to the hand piece, because these parameters change with load on the blade.

The power versus load curve in a generator in a typical ultrasonic surgical system, such as that described in the Thomas patent, has two segments. The first segment has a positive slope of increasing power as the load increases, which indicates constant current delivery. The second segment has a negative slope of decreasing power as the load increases, which indicates a constant or saturated output voltage. The regulated current for the first segment is fixed by the design of the electronic components and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase lock loop locks on to the resonance frequency, continues to monitor the transducer current to voltage phase angle, and maintains the transducer resonating by driving it at the resonance frequency. A key function of such systems is to maintain the transducer resonating across load and temperature changes that vary the resonance frequency. However, these traditional ultrasonic drive systems have little to no flexibility with regards to adaptive frequency control. Such flexibility is key to the system's ability to discriminate undesired resonances. In particular, these systems can only search for resonance in one direction, i.e., with increasing or decreasing frequencies and their search pattern is fixed. The system cannot: (i) hop over other resonance modes or make any heuristic decisions, such as what resonance to skip or lock onto, and (ii) ensure delivery of power only when appropriate frequency lock is achieved.

The prior art ultrasonic generator systems also have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current to voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

Some limited diagnostic tests performed in the past involve sending a signal to the transducer to cause the blade to move and the system to be brought into resonance or some other vibration mode. The response of the blade is then determined by measuring the electrical signal supplied to the transducer when the system is in one of these modes. The ultrasonic system described in U.S. application Ser. No. 09/693,621, filed on Oct. 20, 2000, which is incorporated herein by reference, possesses the ability to sweep the output drive frequency, monitor the frequency response of the ultrasonic transducer and blade, extract parameters from this response, and use these parameters for system diagnostics. This frequency sweep and response measurement mode is achieved via a digital code such that the output drive frequency can be stepped with high resolution, accuracy, and repeatability not existent in prior art ultrasonic systems.

A problem associated with the prior art ultrasonic systems is blade breakage or cracking at points of high stress on the blade. Breakage and cracking of blades are two major causes of the ultrasonic generator failing to acquire lock or failing to maintain longitudinal displacement. For example, as the crack develops both the frequency of oscillation and the magnitude of mechanical impedance change to such an extent that the ultrasonic generator can no longer locate the resonance of the hand piece/blade. A more advanced generator may be able to lock onto a transducer coupled to such a blade. However, a cracked blade has a reduced ability to oscillate in the longitudinal direction. In this situation, an increased ability to locate the desired resonance upon which to lock is not useful, and may actually mask the loss of optimal cutting conditions.

Further, gunked blades, i.e., blades with dried blood, skin, hair and desiccated tissue built up around the blade, present a greater load than clean blades. In particular, the gunk results in a load on the blade, and represents an increase in the mechanical impedance of the transducer presented to the ultrasonic generator.

This phenomenon has the following unwanted consequence. Ultrasonic generators possess a maximum operating voltage beyond which optimal operation of the hand piece/blade is lost. Many ultrasonic drivers attempt to maintain a constant drive current level to the transducer to keep the displacement at the blade tip constant in the presence of varying loads on the blade. As the impedance of the transducer is increased (as a result of tissue pressure, gunked tissue, etc.), the drive voltage must be increased to maintain the drive current at a constant level. Eventually, the loading of the blade becomes great enough such that the voltage reaches a maximum level, and any further loading of the blade results in a reduction of the drive current signal level.

As the current level of the drive signal is reduced, the displacement will begin to fall. The generator can drive an increasing load only as long as the hand piece/blade is not loaded such that the resonance point becomes unrecognizable (due to degradation of the signal to noise ratio or an inability of the hand piece/blade to resonate). As a consequence, the tissue applied force at maximum power, the maximum tissue applied force before losing the resonance signal, and the cutting/coagulating ability of the blade between these two operating points, become degraded.

In addition to the problems associated with loads on the blade, there is a buildup of heat at the coagulum. This buildup absorbs energy from the blade, and heats both the blade and sheath at this location. A cracked or broken blade loses the ability to resonate as well as a blade which is in good condition, and thus should be discarded. However, a gunked blade can be cleaned or used, and resonates as well as a new blade. In an operating room, access to either cracked and gunked blades for visual inspection is not practical. However, it is advantageous to differentiate between broken blades and those which are gunked, but otherwise in good condition, because a user can quickly and with confidence decide whether to discard or to clean an expensive blade. Cleaning a blade which is gunked verses discarding what is otherwise a good blade results in a substantial reduction in purchasing costs which are passed on to hospital patients as a savings.

Impedance measurements of mechanical or acoustic systems obtained at high excitation levels provides much more information than impedance measurements obtained at low excitation levels. Moreover, comparisons of impedance measurements between low and high excitation levels provide even more detailed information about the condition of the hand piece/blade. The condition of the hand piece/blade falls into three main categories.

Figure 1:
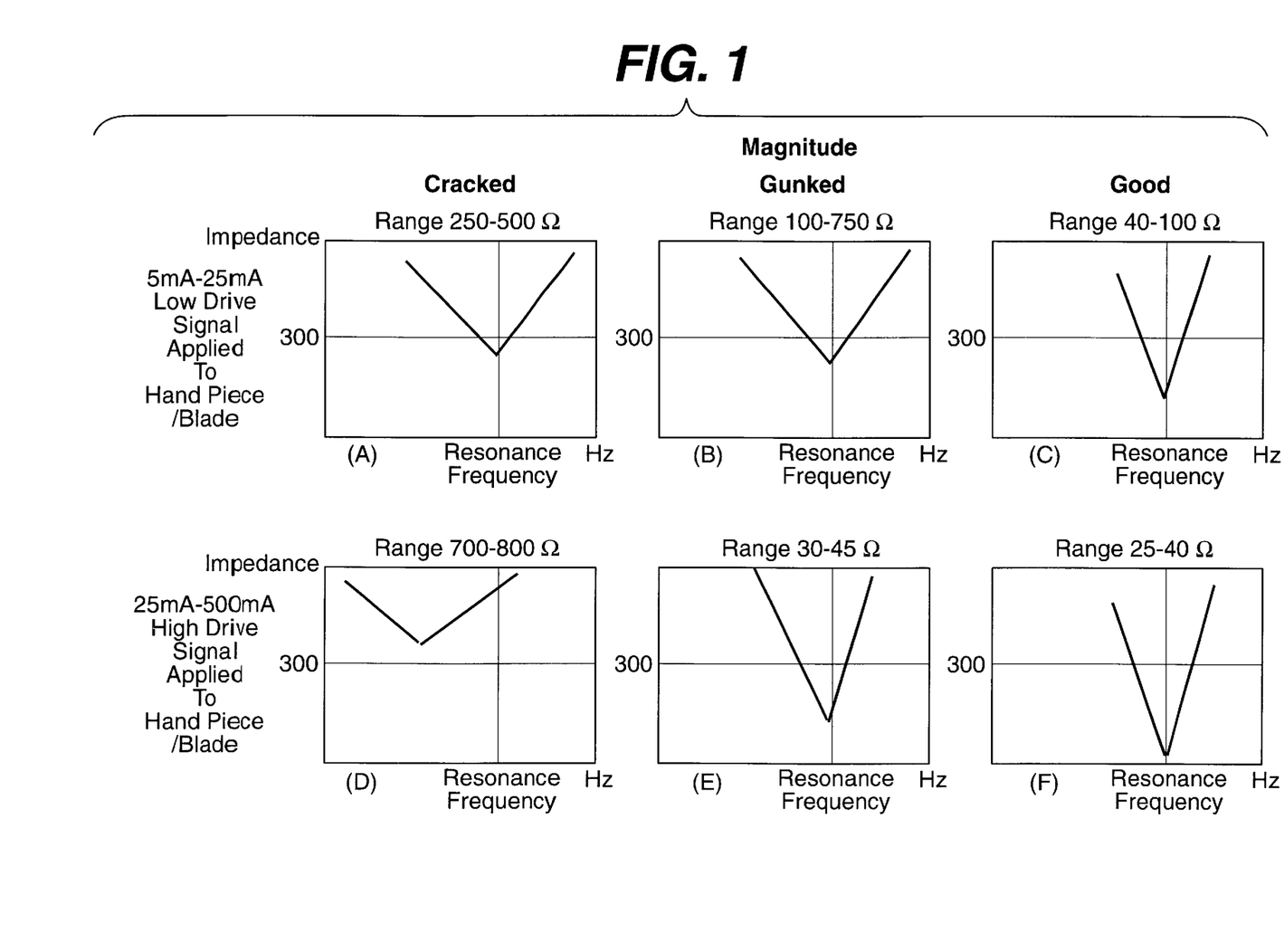
FIG. 1 is an illustration of impedance vs frequency plots for an ultrasonic blade which is cracked, gunked or good when driven at a low signal level or a high signal level.
Figure 2:
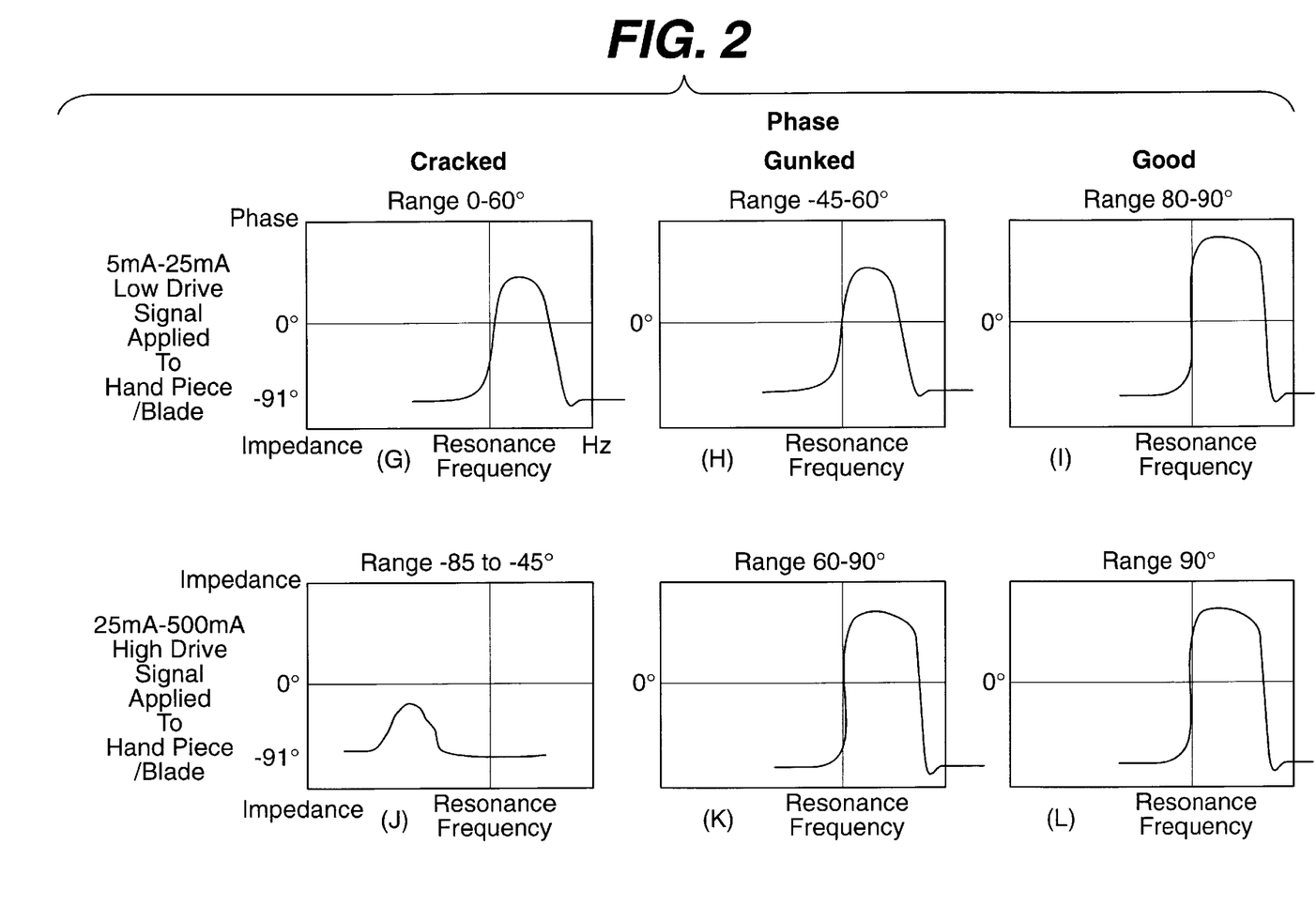
FIG. 2 is an illustration of phase vs frequency plots for an ultrasonic blade which is cracked, gunked or good when driven at a low signal level or a high signal level.

Firstly, gunked blades and new clean blades belong to the same category because silicon anti-node supporters and other mechanical inefficiencies, such as mechanical resistance in the longitudinal direction of the blade, have the same dampening effect as gunk upon the hand piece/blade. In particular, clean/gunked systems become much better resonators as the excitation amplitude is increased, that is they become higher Q systems (the minimum impedance gets markedly lower and the maximum phases get markedly higher; see FIG. 1 and compare the impedance vs. frequency plot shown in B to the impedance vs. frequency plot shown in E, and see FIG. 2 and compare the phase vs. frequency plot shown in H to the phase vs. frequency plot shown in K). The degree of improvement is relative to the loading effect of the gunk involved. As the excitation level changes, there is a minimal change in the resonance frequency which is close to the resonance frequency of a clean hand piece/blade. At a low excitation level, such as 5mA, a cracking or slightly cracked blade is generally self healing and looks very much like a gunked blade (see FIG. 1 and compare the impedance vs. frequency plot shown in A to the impedance vs. frequency plot shown in B, and see FIG. 2 and compare the phase vs. frequency plot shown in G to the phase vs. frequency plot shown in H). The self healing characteristic, in which at a molecular level the blade becomes more homogeneous if not overly excited, results in an optimally tuned system. At low excitation levels, the surfaces at the interface of the crack do not behave like disjoint surfaces, and are held in close contact to each other by the parts of the blades which are still intact. In this situation, the system appears "healthy."

Secondly, at larger excitation levels, such as 25 mA or greater, stresses at the crack become large enough such that the portion of the blade which is distal to the crack no longer acts as if it is intimately connected to the proximal portion of the blade. A characteristic of these hand piece/blades is their non-linear behavior (i.e., very sharp non-continuous changes in impedance magnitudes and phase) which occur as the resonance frequency is approached and the stresses in the shaft of the hand piece become large. As the frequency approaches resonance of the "intact blade", the stresses become increasingly greater until at a certain point the blade suddenly becomes disjointed at the crack. This effectively shortens the blade, and the resonator or blade will possess completely different resonance impedance characteristics. Typically, the impedance of such a shorter blade results in a hand piece/blade which possesses a lower Q, as well as a lower frequency of resonance (see FIG. 1 and compare the respective impedance vs. frequency plots shown in A and C to the respective impedance vs. frequency plots shown in D and F, and see FIG. 2 and compare the respective phase vs. frequency plots shown in G and I to the respective phase vs. frequency plots shown in J and L).

Figure 3:
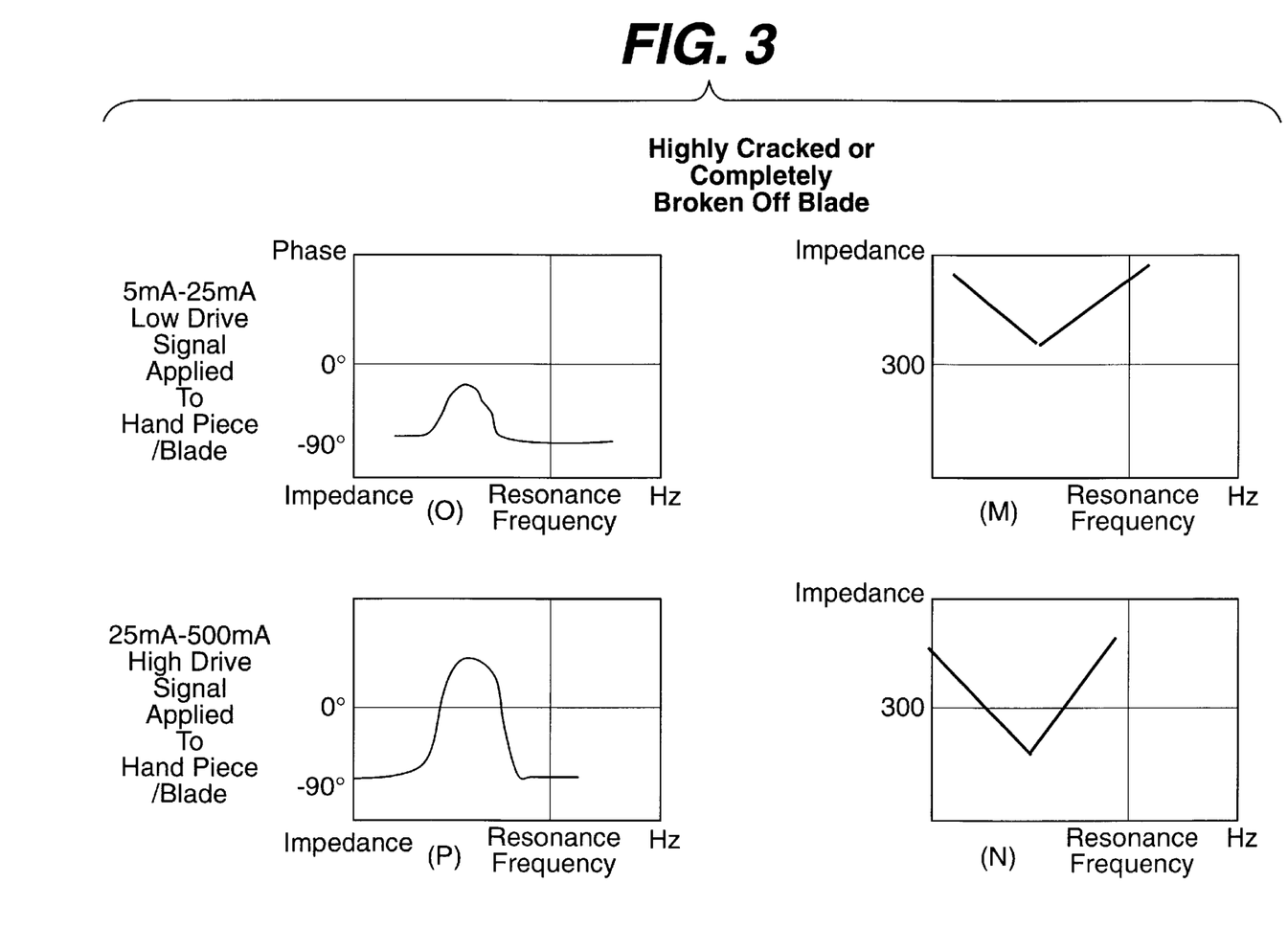
FIG. 3 is an illustration of impedance vs frequency plots for an ultrasonic blade which is cracked or has completely broken away from a hand piece when driven at a low signal level or a high signal level.

Lastly, severely cracked blades include, but are not limited to, blades having tips which have completely fallen off due to mechanical stress acting on the blades. These blades are substantially equivalent to gunked blades. However, they are not useful for cutting/coagulating tissue in longitudinal directions. Such blades appear to behave similarly in that they present improved (if only marginally) impedance characteristics at higher excitation levels, and their frequency of resonance is not affected by higher excitation levels. However, they can be differentiated from gunked blades due to their extremely high impedance level. This requires absolute measurements, but only coarse levels of precision are required. Generally, the resonance frequency of the transducer or blade is shifted far away from the normal resonance that is typically used for a specific ultrasonic system. This shift is usually a downward shift of the resonance frequency of about 2 kilohertz. When excited with a higher level of current and compared with a lower level of current, the impedance magnitude, resonance frequency and maximum phase at resonance are quantitatively far different than the corresponding characteristics of blades which are only gunked (see FIG. 3 and compare the impedance vs. frequency plot shown in M to the impedance vs. frequency plot shown in N, and compare the phase vs. frequency plot shown in O to the phase vs. frequency plot shown in P). In this case, the hand piece/blade typically possesses a magnitude of impedance at resonance which is approximately 400 ohms higher for cracked blades than that of heavily gunked but otherwise good blades.

Most broken or cracked blades have selfhealing characteristics associated with them. The self healing characteristic, in which at a molecular level the blade becomes more homogeneous if not overly excited, results in an optimally tuned system. This homogeneity is disturbed at a high excitation level, resulting in an untuned system. When cracked or broken blades are un-energized for an extended period of time, or if energized at a low intensity for a period of time, such blades present a mechanical impedance to the ultrasonic generator that is closer to the mechanical impedance which is exhibited by an unbroken blade. At high excitation levels, the portion of the blade distal to the crack is no longer intimately connected to the hand piece/blade. The effect of the high excitation level upon the blade is that the portion of the blade proximal to the crack "bangs" against the portion of the blade distal to the crack, which causes a loading effect which is greater than the loading effect at low excitation displacement levels.

In other words, in the frequency range of approximately 1,000 Hz, centered around the resonance frequency of an unbroken blade, the same type of broken blade will exhibit one impedance sweep characteristic at a low voltage excitation of the drive transducer and another at a high voltage excitation level. In contrast, an unbroken blade exhibits the same impedance at both excitation levels, as long as the impedance measurement is performed quickly enough, or at a low enough displacement level such that the transducer or the blade does not overheat. Heat causes the resonance point to shift downwards in frequency. This heating effect is most prevalent when the magnitude of the excitation frequency approaches the resonance frequency due to gunk.

In addition, an excitation threshold exists, below which the blade "self heals" and presents increasingly "tuned" impedance levels (over time) to the driving elements, and above which the crack presents a discontinuity to the homogeneity of the blade. Thus, below this threshold, the impedance characteristic may exhibit the same characteristic for all excitation levels. The blade may also appear to be healing itself at these lowered excitation levels. Above this excitation threshold, the impedance may possess a different appearance than the low impedance measurements, but may still not change with increasing levels of excitation. This excitation threshold is different for each type of blade as well as each cracked location on the blade, and is modulated by the amount of gunk loading the distal part of the blade.

Some of the impedance differences seen in a system containing a broken blade (which are not seen in a system containing an unbroken blade), when first driven with a low excitation current and then with a high excitation current, are a lower Q (i.e., a lower minimum impedance) over a frequency span centered about the resonance frequency of an unbroken blade, i.e., a higher minimum impedance and/or a lower maximum impedance. It could also mean a higher "phase margin", i.e., Fa-Fr (where Fa-Fr is anti-resonance frequency minus the resonance frequency, respectively). Other differences are a higher impedance at a frequency slightly above the anti-resonance frequency of the normally operating system, a higher impedance at a frequency slightly below the resonance point of a properly working system, or a large change in the resonance frequency. Gunked or loaded blades connected to a drive system exhibit somewhat opposite effects to that of a cracked blade. A system loaded in this manner exhibits an increasingly improved Q around the resonance point as the excitation voltage is increased.

Previous attempts to differentiate between gunked and cracked blades have been based on one of two theories. First, there is a set of resonant frequencies and magnitudes of impedances which can be tabulated and used to uniquely classify each type of situation in question (broken verses gunk blades, etc.). Second, there is an impedance signature characteristic of each family of blades which can be programmed into the generator for recognition purposes. These approaches, however, require large computations of data. Complicating the factors which need to be considered are: the many types of blades presently in use and the future blades which may be developed, the quickly changing temperature of the blades and/or the hand pieces during use, the age of the piezo-electric material, the self healing affect over time of slightly cracked blades and the requirement for an absolute impedance measurement which requires expensive and complicated measurement equipment which must be kept calibrated. Another complicating factor is the simulation and recordation of the impedance characteristics of all the different types of cracks on each blade which simulate the effects of gunk. These complications make it impossible, or at least impractical, to implement a tabulation/recognition methodology for use with present ultrasonic systems.

Detection of debris on the blade, and the determination of the condition of tissue that the blade is in contact with are additional problems associated with conventional ultrasonic systems. Some ultrasonic blades are equipped with a sheath which covers the blade. The majority of the sheath is not in contact with the blade. Space (voids) between the sheath and the blade permits the blade to move freely. During use, this space can become filled with debris such as blood and tissue. This debris has a tendency to fill the space between the sheath and blade, and increase mechanical coupling between the blade and the sheath. As a result, undesired loading of the blade may increase, the temperature of the blade sheath may increase and the energy delivered to the tip may be reduced. In addition, if the debris sufficiently coagulates/hardens inside the sheath, the ability of the generator to initiate blade vibration while in contact with tissue may be prohibited. Moreover, vibration/start up of the blade in free air may also be inhibited. It is also desirable to know the relative condition of skin tissue, especially the condition of the tissue which has been altered by ultrasonic energy. Assessing the condition of tissue permits the proper adjustment of the energy applied to the tissue, and also permits the indication of when adequate cauterization, dessication, or other tissue effects have occurred. Together, these provide a means to determine whether additional energy or whether an extension of the application time of the energy is required. Further, the assessment of the tissue condition permits the avoidance of insufficient energy applications and insufficient tissue effects (i.e., poor tissue coagulation or poor tissue cauterization), which prevent application of excessive amounts of ultrasonic energy to the skin tissue which can harm surrounding tissue in the area of blade usage.

There are other problems associated with the conventional ultrasonic surgical systems. For instance, an insufficient application of torque to the blade when mounting it to a hand piece can cause squealing and prevent the ultrasonic generator from acquiring lock, prevent transmission of energy to the area of the patient being treated, or lead to a large amount of energy dissipation at the loose interface of the hand piece and blade, which cause a degradation of the overall performance of the system and the generation of unwanted heat. Similar symptoms are also associated with broken blades and/or gunked blades, i.e., blades that have become clogged or loaded with debris, such as blood and tissue.

Figure 4:
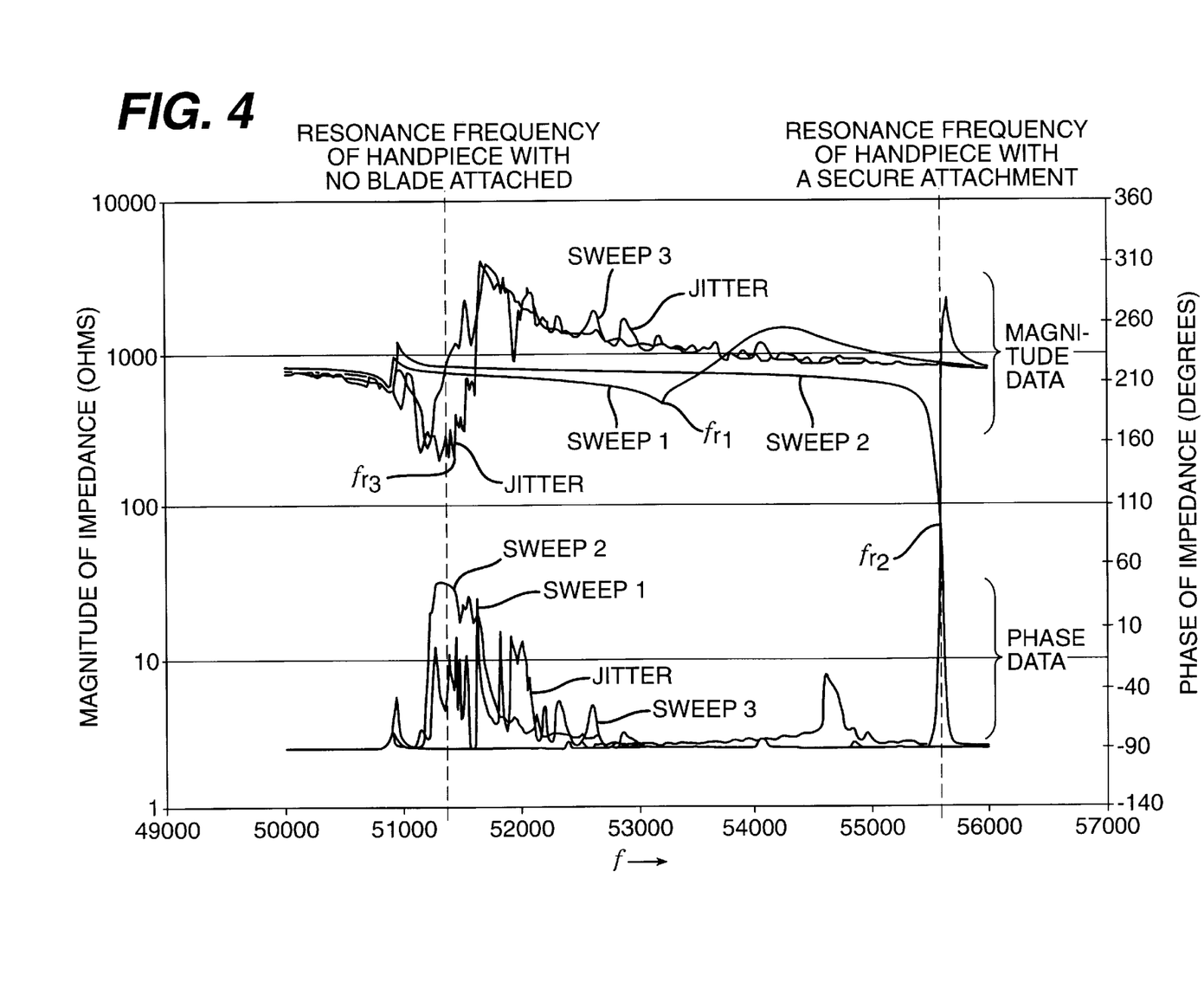
FIG. 4 is a graphical plot illustrating jitter in a resonance measurement of the hand piece/blade.

When a high drive current is used to excite the blade, a loose connection will produce a "jittery" impedance response as shown in FIG. 4, where $f_{r1}$ is a resonance frequency associated with a first frequency sweep, $f_{r2}$ is a resonance frequency associated with a second frequency sweep and $f_{r3}$ is a resonance frequency associated with a third frequency sweep. This occurs as a result of the change in mechanical integrity of an attachment, such as a blade, which in turn causes the blade to become more tightly or less tightly connected to the hand piece. As a result, each time the drive signal is swept through the applicable frequency range, a different frequency of resonance is measured, and the magnitude and phase of impedance measurements appears "noisy".

The squealing, heating and loss of tissue effects associated with a loose blade is repaired by tightening the blade. Accordingly, it is desirable to differentiate the occurrence of faults associated with a loose blade from other more serious faults (e.g., a broken blade or debris loaded blade). It is therefore apparent that there is a need for a method for identifying the occurrence of a loose blade in a hand piece to permit rapid repairs to the ultrasonic system.

SUMMARY OF THE INVENTION

The present invention is a method for detecting loose blades in a hand piece connected to an ultrasonic surgical system. Generally, impedance measurements which are obtained at high excitation levels provide a greater amount of information than impedance measurements which are obtained at low excitation levels. In accordance with the invention, to detect a loose connection, a number of frequency sweeps of a drive signal is performed through a range which includes the resonance of a hand piece/blade system and the resonance of the hand piece without a blade attached. The frequencies of resonance in each sweep are compared. A substantial difference between the frequency sweeps is indicative of a loose blade, and a "Tighten Blade" message is displayed on a liquid crystal display on the ultrasonic generator console.

In an alternative embodiment of the invention, the RMS noise in the magnitude of the impedance spectrum and/or phase in the impedance spectrum is measured. A large noise value is an indication that the blade is improperly attached to the hand piece.

The invention permits rapid and easy diagnosis of loose blade connections. The method of the invention also assists a surgeon or nurse in knowing when to tighten the blade, as opposed to performing more lengthy and detailed diagnostic or cleaning procedures. In addition, the time and costs associated with the diagnostic procedures to isolate faults are eliminated because, upon determining that the blade is not loose, the surgeon and nurse can request a new blade based on the assumption that the blade is broken.

BRIEF DESCRIPTION OF THE DRAWINGS

The foregoing and other advantages and features of the invention will become more apparent from the detailed description of the preferred embodiments of the invention given below with reference to the accompanying drawings in which.

DETAILED DESCRIPTION OF THE PREFERRED EMBODIMENTS

Figure 5:
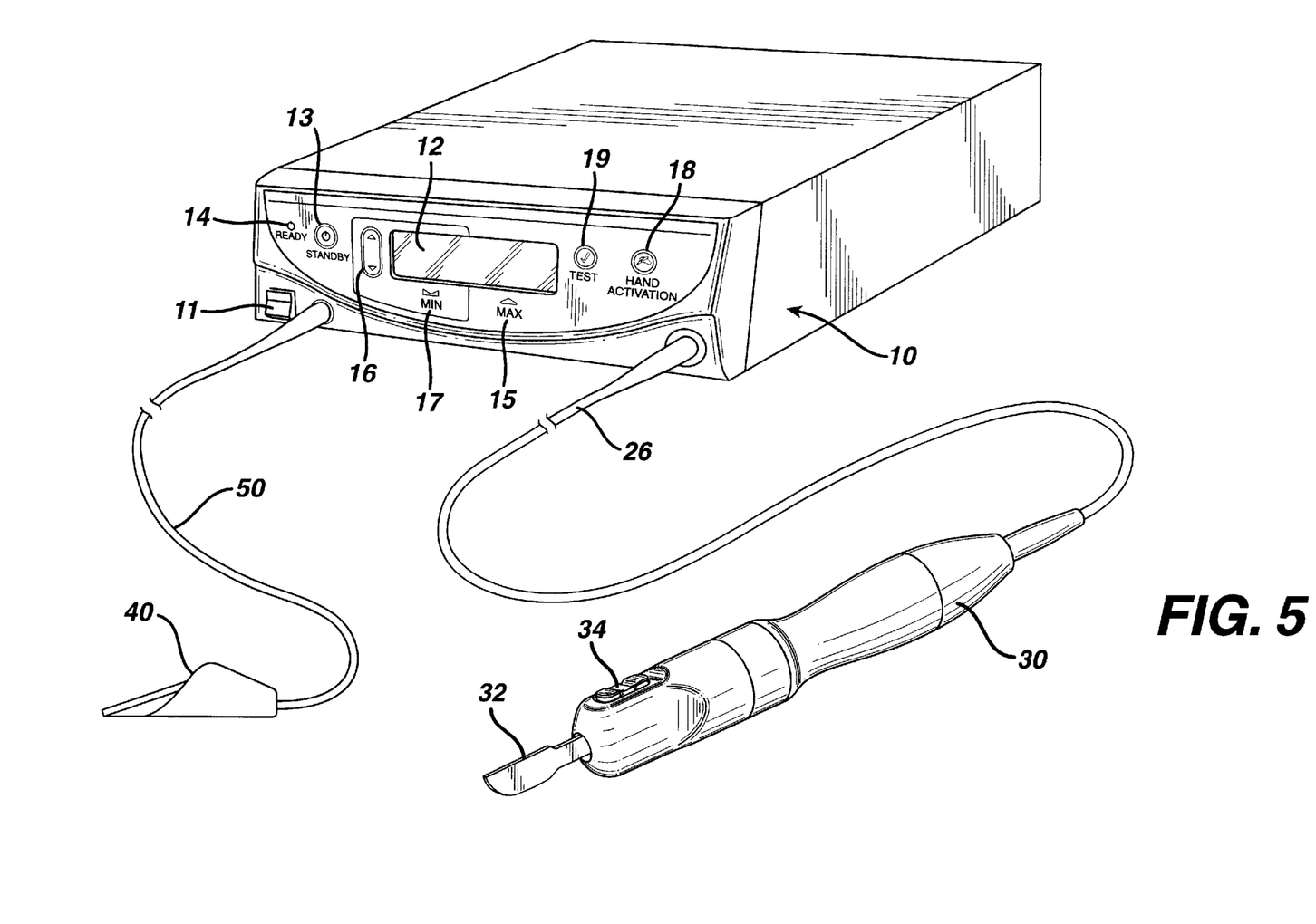
FIG. 5 is an illustration of a console for an ultrasonic surgical cutting and hemostasis system, as well as a hand piece and foot switch in which the method of the present invention is implemented.

FIG. 5 is an illustration of a system for implementing the method according to the invention. By means of a first set of wires in cable 20, electrical energy, i.e., drive current, is sent from the console 10 to a hand piece 30 where it imparts ultrasonic longitudinal movement to a surgical device, such as a sharp scalpel blade 32. This blade can be used for simultaneous dissection and cauterization of tissue. The supply of ultrasonic current to the hand piece 30 may be under the control of a switch 34 located on the hand piece, which is connected to the generator in console 10 via wires in cable 20. The generator may also be controlled by a foot switch 40, which is connected to the console 10 by another cable 50. Thus, in use a surgeon may apply an ultrasonic electrical signal to the hand piece, causing the blade to vibrate longitudinally at an ultrasonic frequency, by operating the switch 34 on the hand piece with his finger, or by operating the foot switch 40 with his foot.

The generator console 10 includes a liquid crystal display device 12, which can be used for indicating the selected cutting power level in various means such, as percentage of maximum cutting power or numerical power levels associated with cutting power. The liquid crystal display device 12 can also be utilized to display other parameters of the system. Power switch 11 is used to turn on the unit. While it is warming up, the "standby" light 13 is illuminated. When it is ready for operation, the "ready" indicator 14 is illuminated and the standby light goes out. If the unit is to supply maximum power, the MAX button 15 is depressed. If a lesser power is desired, the MIN button 17 is activated. The level of power when MIN is active is set by button 16.

When power is applied to the ultrasonic hand piece by operation of either switch 34 or 40, the assembly will cause the surgical scalpel or blade to vibrate longitudinally at approximately 55.5 kHz, and the amount of longitudinal movement will vary proportionately with the amount of driving power (current) applied, as adjustably selected by the user. When relatively high cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate of the surgeon, the nature of the tissue type and the vascularity of the tissue.

Figure 6:
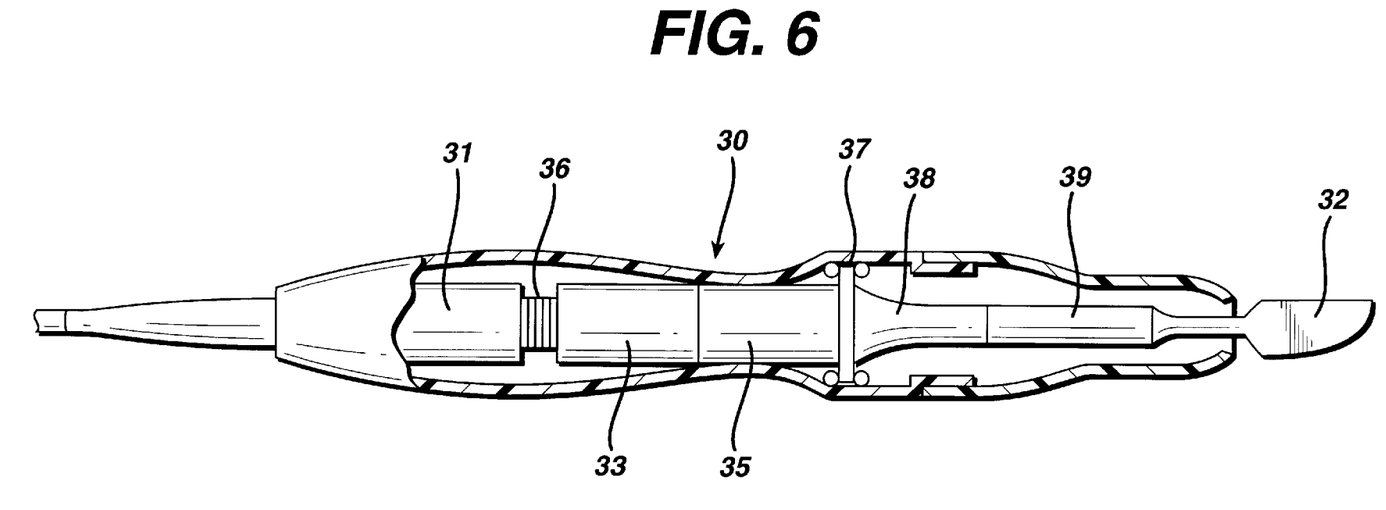
FIG. 6 is a schematic view of a cross section through the ultrasonic scalpel hand piece of the system of FIG. 5.

As illustrated in more detail in FIG. 6, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements with a motion null point located at some point along the stack. The transducer stack is mounted between two cylinders 31 and 33. In addition a cylinder 35 is attached to cylinder 33, which in turn is mounted to the housing at another motion null point 37. A horn 38 is also attached to the null point on one side and to a coupler 39 on the other side. Blade 32 is fixed to the coupler 39. As a result, the blade 32 will vibrate in the longitudinal direction at an ultrasonic frequency rate with the transducer 36. The ends of the transducer achieve maximum motion with a portion of the stack constituting a motionless node, when the transducer is driven with a maximum current at the transducers' resonant frequency. However, the current providing the maximum motion will vary with each hand piece and is a valve stored in the non-volatile memory of the hand piece so the system can use it.

The parts of the hand piece are designed such that the combination will oscillate at the same resonant frequency. In particular, the elements are tuned such that the resulting length of each such element is one-half wavelength. Longitudinal back and forth motion is amplified as the diameter closer to the blade 32 of the acoustical mounting horn 38 decreases. Thus, the horn 38 as well as the blade/coupler are shaped and dimensioned so as to amplify blade motion and provide harmonic vibration in resonance with the rest of the acoustic system, which produces the maximum back and forth motion of the end of the acoustical mounting horn 38 close to the blade 32. A motion at the transducer stack is amplified by the horn 38 into a movement of about 20 to 25 microns. A motion at the coupler 39 is amplified by the blade 32 into a blade movement of about 40 to 100 microns.

Figure 7A:
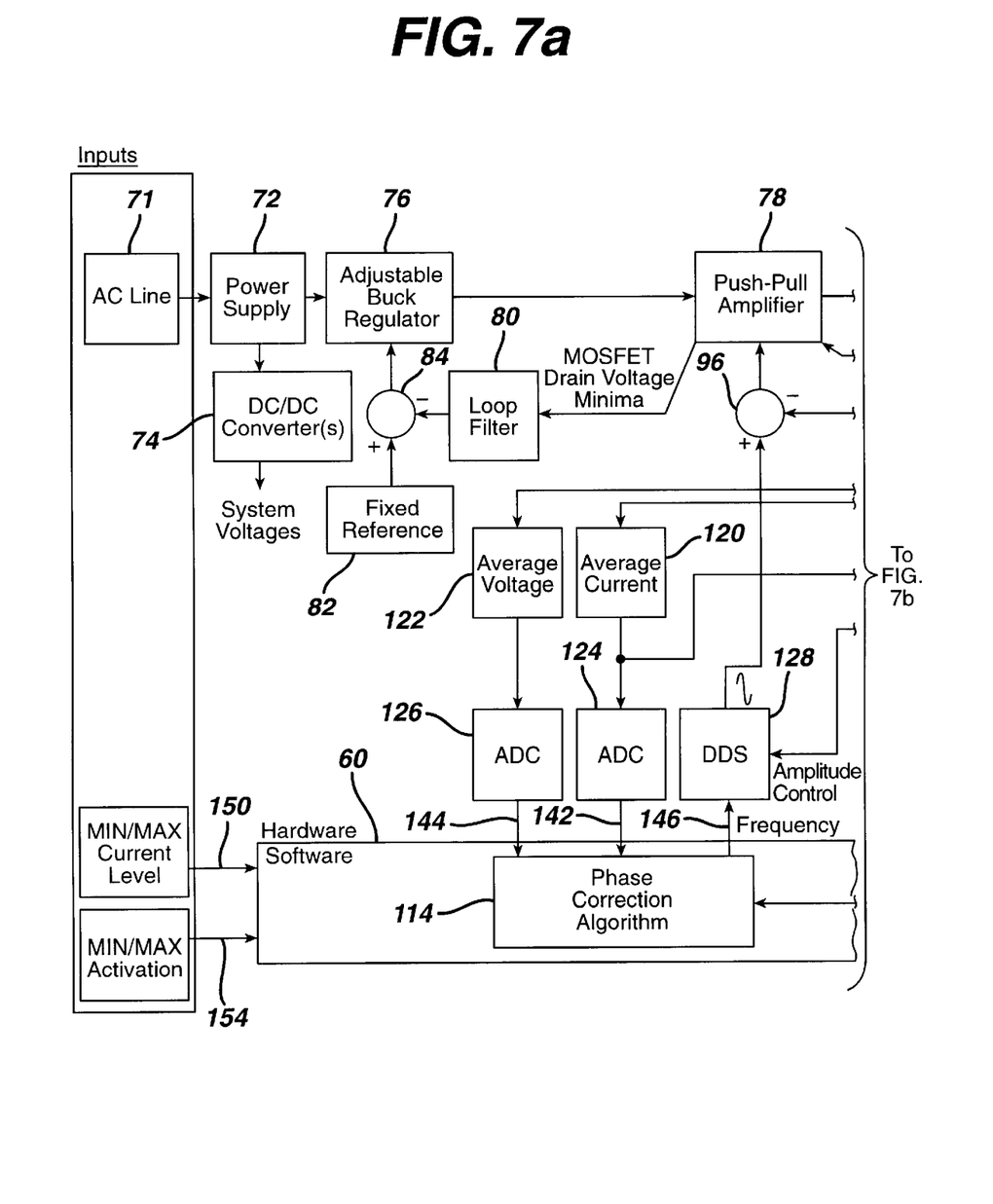
FIGS. 7(a) and 7(b) are block diagrams illustrating the ultrasonic generator for implementing the method of the invention.
Figure 7B:
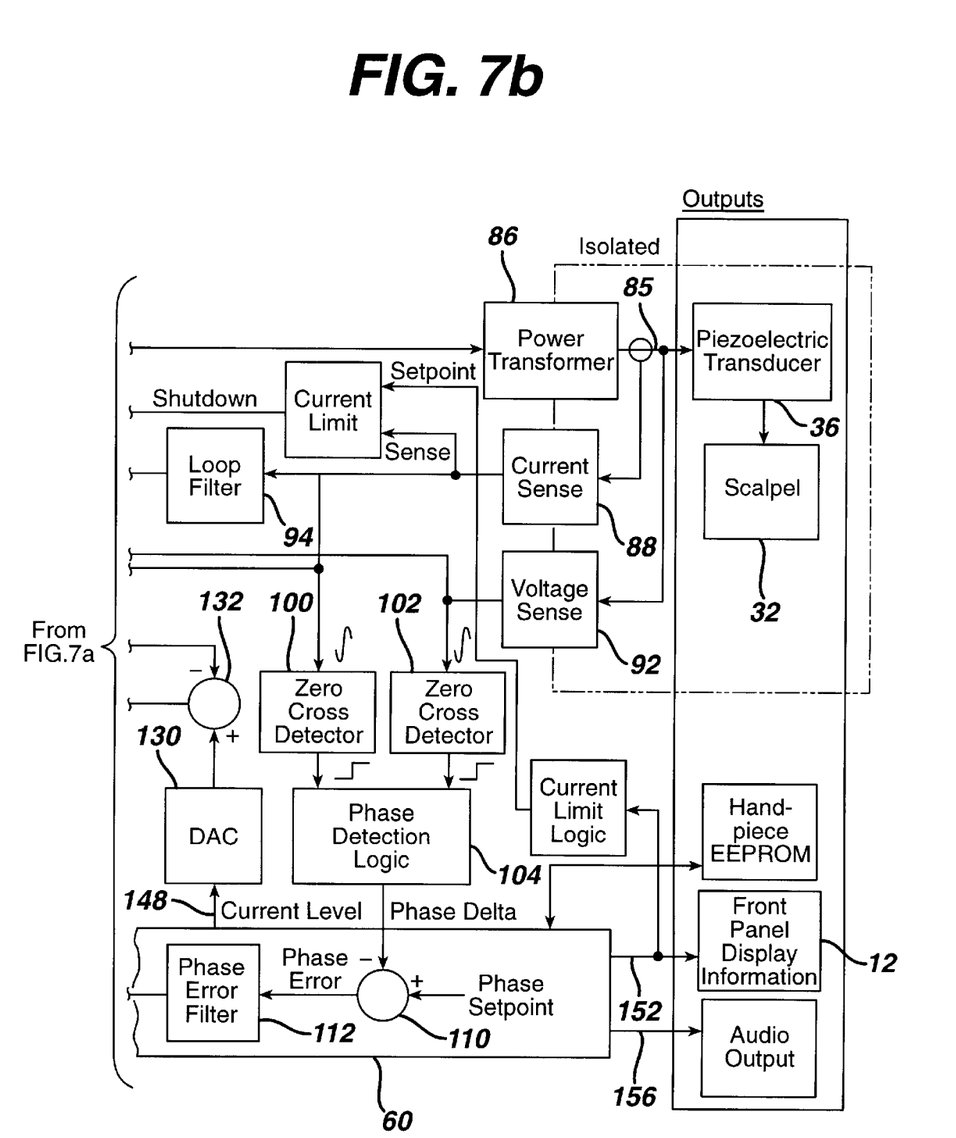

The system which creates the ultrasonic electrical signal for driving the transducer in the hand piece is illustrated in FIGS. 7(a) and 7(b). This drive system is flexible and can create a drive signal at a desired frequency and power level setting. A DSP 60 or microprocessor in the system is used for monitoring the appropriate power parameters and vibratory frequency as well as causing the appropriate power level to be provided in either the cutting or coagulation operating modes. The DSP 60 or microprocessor also stores computer programs which are used to perform diagnostic tests on components of the system, such as the transducer/blade.

For example, under the control of a program stored in the DSP or microprocessor 60 such as a phase correction algorithm, the frequency during startup can be set to a particular value, e.g., 50 kHz. It can than be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the program can decrease the increment, e.g., to 25 cycles which both can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is a undesired resonant mode, e.g., at say 51 kHz, the program can cause the frequency to sweep down, e.g., from 60 kHz, to find resonance. Also, the system can sweep up from 50 kHz and hop over 51 kHz where the undesired resonance is located. In any event, the system has a great degree of flexibility.

In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 7(b)) to the console front panel display 12. Further, the DSP or microprocessor 60 generates a digital current level signal 148 that is converted to an analog signal by digital-to-analog converter (DAC) 130. The resulting reference analog signal is applied as a current set point to summing node 132. A signal representing the average output current from circuit 120 is applied to the negative input of node 132. The output of node 132 is a current error signal or amplitude control signal which is applied to direct digital synthesis (DDS) circuit 128 to adjust the amplitude of its output, as opposed to the frequency of its output, which is controlled by the signal on line 146 from the DSP or microprocessor 60. The arrangement of current level signal 148, DAC 130, summing node 130, and signal supplied by average output voltage 122 allows the DSP or microprocessor 60 to adjust the output current such that it can generate a desired power versus load curve when not in constant current mode.

To actually cause the surgical blade to vibrate, the user activates the foot switch 40 or the hand piece switch 34. This activation puts a signal on line 154 in FIG. 7(a). This signal is effective to cause power to be delivered from push-pull amplifier 78 to the transducer 36. When the DSP or microprocessor 60 has achieved lock on the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

Figure 8:
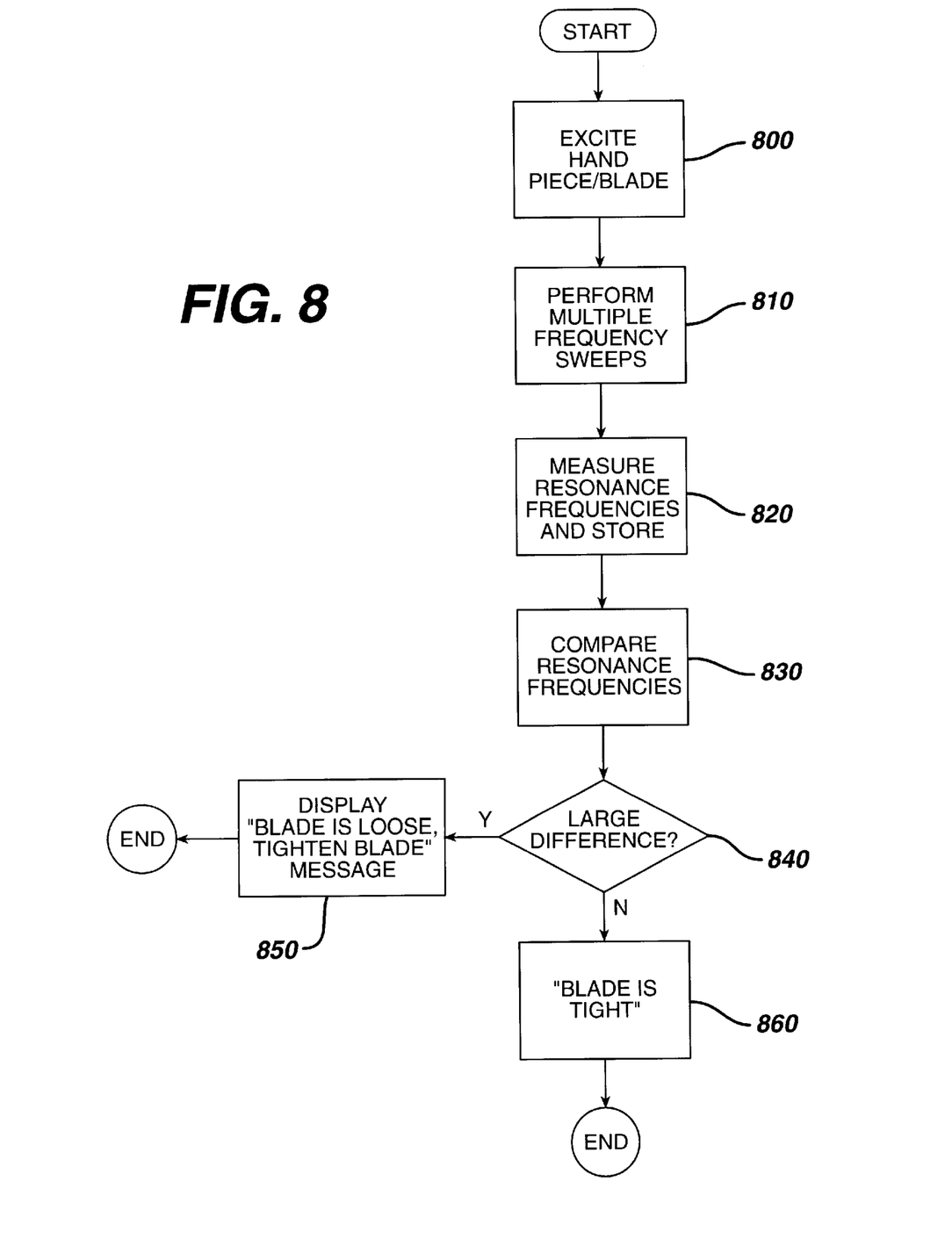
FIG. 8 is a flow chart illustrating a preferred embodiment of the method of the invention.

FIG. 8 is a flow chart illustrating a preferred embodiment of the method of the invention. Under control of the program stored in the DSP or microprocessor 60 of the system shown in FIGS. 7(a) and 7(b), the method of the invention is implemented by using the ultrasonic generator to excite the hand piece/blade at a high excitation level, such as 425 mA, as indicated in step 800. A higher excitation level is used because a low level signal may not cause the appearance of any jitter which is present. Approximately three frequency sweeps are performed from the typical frequency resonance range of a hand piece without a blade attachment to the typical frequency resonance range of a hand piece with a blade attachment to determine the frequencies at which minimum impedance occurs, as indicated in step 810. In the preferred embodiment, the range is from 50 kHz to 56 kHz.

A number of resonance frequencies are measured and stored, as indicated in step 820. In the preferred embodiment, three resonance frequencies at which the minimum impedance occurs are recorded and stored (for example, three resonance values associated with three minimum impedances and three minimum phases). Next, as indicated in step 860, a comparison of the stored impedance values is performed to determine whether a large difference exists between the stored resonance frequencies in accordance with the relationship:

$$(|f_1-f_2|+|f_2-f_3|+|f_3-f_1|)>20 \text{ Hz}, \quad \text{Eq. 1}$$

where $f_1$ is the first measured resonance frequency, $f_2$ is the second measured resonance frequency and $f_3$ is the third measured resonance frequency.

If the calculated frequency value in Eq. 1 is greater than 20 Hz, the blade is loose, and a "Tighten Blade" message is displayed on the LCD, as indicated in step 850. If a large difference does not exists between the stored resonance frequencies, then the hand piece is tight, and the diagnostic test is terminated, as indicated in step 860.

In order to obtain the impedance measurements and phase measurements, the DSP 60 and the other circuit elements of FIGS. 7(a) and 7(b) are used. In particular, push-pull amplifier 78 delivers the ultrasonic signal to a power transformer 86, which in turn delivers the signal over a line 85 in cable 26 to the piezoelectric transducers 36 in the hand piece. The current in line 85 and the voltage on that line are detected by current sense circuit 88 and voltage sense circuit 92. The current and voltage sense signals are sent to average voltage circuit 122 and average current circuit 120, respectively, which take the average values of these signals. The average voltage is converted by analog-to-digital converter (ADC) 126 into a digital code that is input to DSP 60. Likewise, the current average signal is converted by analog-to-digital converter (ADC) 124 into a digital code that is input to DSP 60. In the DSP the ratio of voltage to current is calculated on an ongoing basis to give the present impedance values as the frequency is changed. A significant change in impedance occurs as resonance is approached.

The signals from current sense 88 and voltage sense 92 are also applied to respective zero crossing detectors 100, 102. These produce a pulse whenever the respective signals cross zero. The pulse from detector 100 is applied to phase detection logic 104, which can include a counter that is started by that signal. The pulse from detector 102 is likewise applied to logic circuit 104 and can be used to stop the counter. As a result, the count which is reached by the counter is a digital code on line 104, which represents the difference in phase between the current and voltage. The size of this phase difference is also an indication of resonance. These signals can be used as part of a phase lock loop that cause the generator frequency to lock onto resonance, e.g., by comparing the phase delta to a phase set point in the DSP in order to generate a frequency signal to a direct digital synthesis (DDS) circuit 128 that drives the push-pull amplifier 78.

Further, the impedance and phase values can be used as indicated above in a diagnosis phase of operation to detect if the blade is loose. In such a case the DSP does not seek to establish phase lock at resonance, but rather drives the hand piece at particular frequencies and measures the impedance and phase to determine if the blade is tight.

Figure 9:
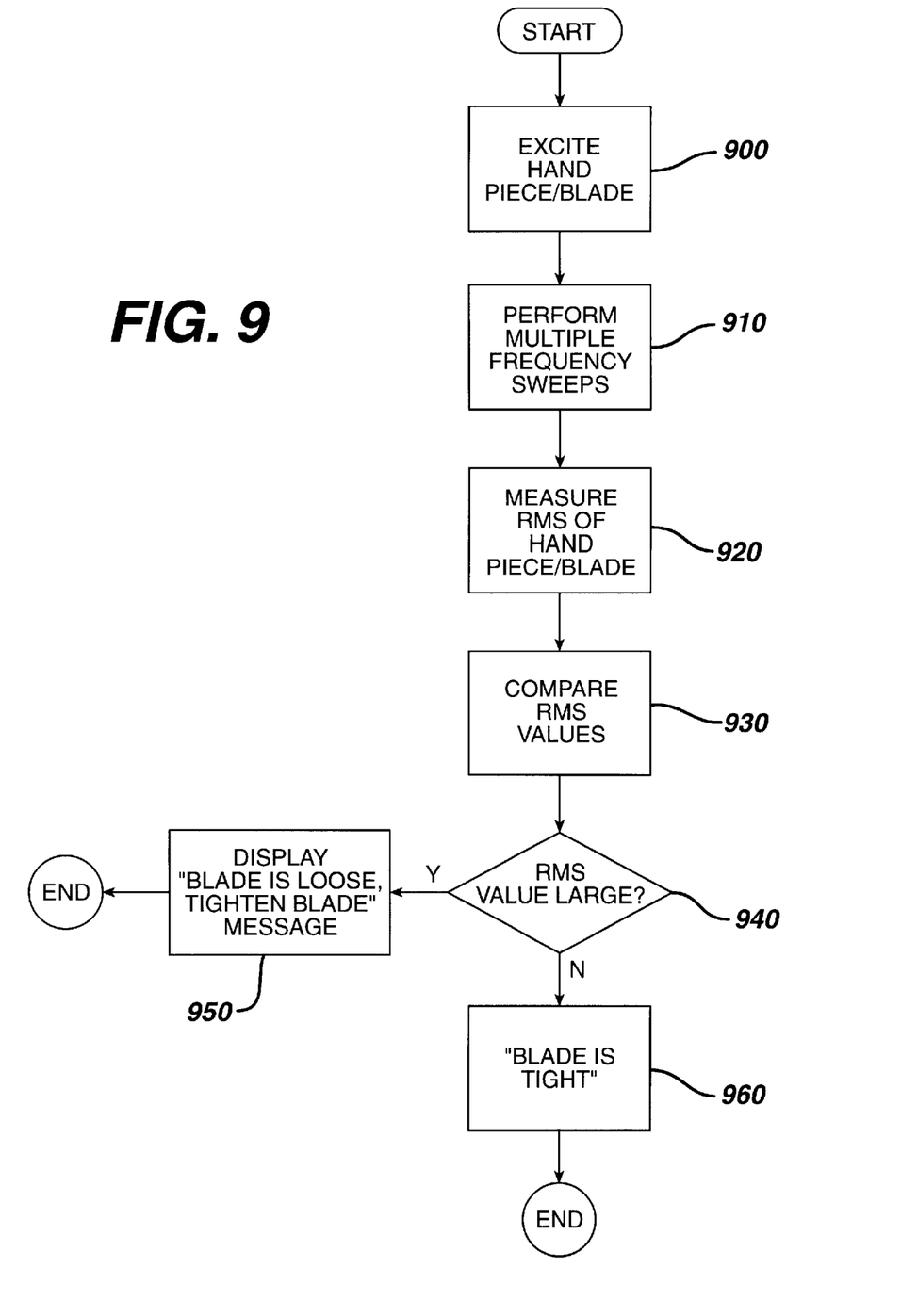
FIG. 9 is a flow chart illustrating an alternative embodiment of the method of the invention.

FIG. 9 is a flow chart illustrating an alternative embodiment of the method of the invention. Under control of the program stored in the DSP or microprocessor 60, the ultrasonic generator is used to excite the hand piece/blade at a high excitation level, such as 425 mA, as indicated in step 900. Approximately three frequency sweeps are performed in the range of 50 kHz to 56 kHz and the frequencies at which minimum impedance occurs are determined, as indicated in step 910.

A number of resonance frequencies are measured and stored, as indicated in step 920. In the preferred embodiment, three resonance frequencies at which the minimum impedance occurs are recorded and stored, as indicated in step 930. Next, the calculation in accordance with the relationship described in Eq. 1 is performed to determine whether a loose connection exists, as indicated in step 940. Alternatively, the RMS noise of the phase or magnitude of the impedance is calculated by DSP 60. A large noise value is an indication that the blade is improperly attached to the hand piece.

If the calculated frequency value is greater than 20 Hz, the blade is loose, and a "Tighten Blade" message is displayed on the LCD 12, as indicated in step 950. If the calculated frequency value is less than 25 Hz, then the hand piece is tight, and the diagnostic test is terminated, as indicated in step 960. In an embodiment, a "Blade is Tight" message is display prior to terminating the diagnostic test.

Of note, if a broken or gunked blade is present, the difference in frequencies would be small, and therefore no jitter would be present in the frequency plots shown in FIG. 4. This would be indicative of the need to perform more lengthy and detailed tests, which the present invention ensures the necessity for due to the ability to detect loose blade connections which exhibit the symptoms associated with broken or gunked blades.

Using the method of the invention, a rapid and easy diagnose of a loose blade connection is achieved. The method of the invention also assists a surgeon or nurse in knowing when to tighten the blade, as opposed to performing a more lengthy and detailed diagnostic procedure. In addition, the method of the invention eliminates the additional costs associated with diagnostic procedures because, upon determining that the blade is not lose, the surgeon and nurse can request a new blade based on the assumption that the blade is broken.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for detecting a loose blade in a hand piece connected to an ultrasonic surgical system, comprising the steps of:

exciting the hand piece with a high level drive signal using an ultrasonic generator;

performing multiple frequency sweeps of the hand piece across a predetermined frequency range;

measuring resonance frequencies of the hand piece during the multiple frequency sweeps at which minimum impedance of the hand piece occur;

storing the measured resonance frequencies of the hand piece at which minimum impedance occurs;

comparing the stored resonance frequencies to determine whether a difference between the stored resonance frequencies exceeds a predetermined threshold; and if the difference between the stored resonance frequencies exceeds the predetermined threshold, displaying a message on a liquid crystal display of the generator.

2. The method of claim 1, wherein the drive signal has a current level of 425 mA.

3. The method of claim 1, wherein three frequency sweeps across the predetermined frequency range are performed.

4. The method of claim 3, wherein the predetermined range is from 50 kHz to 56 kHz.

5. The method of claim 1, wherein said measuring step comprises the step of:

measuring three resonance values at which minimum impedance occurs.

6. The method of claim 5, wherein three minimum impedances and three minimum phases are associated with the three resonance values at which minimum impedance occurs.

7. The method of claim 1, wherein said comparing the stored resonance frequencies comprises the step of:

calculating a difference value in accordance with the relationship $(|f_1-f_2|+|f_2-f_3|+|f_3-f_1|)$, wherein $f_1$ is a first measured resonance frequency, $f_2$ is a second measured resonance frequency and $f_3$ is a third measured resonance frequency.

8. The method of claim 7, further comprising the step of:

determining whether the difference value exceeds the predetermined threshold.

9. The method of claim 8, wherein the predetermined threshold is approximately 20 Hz.

10. The method of claim 1, wherein the step of displaying the message comprises the step of:

displaying a "Tighten Blade" message on the liquid crystal display.

* * * * *